United States Patent
Owoc

(10) Patent No.: US 11,278,516 B2
(45) Date of Patent: Mar. 22, 2022

(54) MEDICINAL COMPOSITIONS OF CANNABINOIDS AND XANTHINES

(71) Applicant: John H Owoc, Weston, FL (US)

(72) Inventor: John H Owoc, Weston, FL (US)

(73) Assignee: COGNITIVE IP HOLDINGS, LLC, Weston, FL (US)

( * ) Notice: Subject to any disclaimer, the term of this patent is extended or adjusted under 35 U.S.C. 154(b) by 0 days.

(21) Appl. No.: 16/541,731

(22) Filed: Aug. 15, 2019

(65) Prior Publication Data

US 2021/0046039 A1 Feb. 18, 2021

(51) Int. Cl.
| | |
|---|---|
| *A61K 31/352* | (2006.01) |
| *A61K 31/05* | (2006.01) |
| *A61K 9/00* | (2006.01) |
| *A61K 31/522* | (2006.01) |

(52) U.S. Cl.
CPC .......... *A61K 31/352* (2013.01); *A61K 9/0095* (2013.01); *A61K 31/05* (2013.01); *A61K 31/522* (2013.01)

(58) Field of Classification Search
CPC .... A61K 31/05; A61K 9/0053; A61K 9/0095; A61K 9/14; A61K 31/4375; A61K 31/522; A61P 25/28
See application file for complete search history.

(56) References Cited

U.S. PATENT DOCUMENTS

2016/0324777 A1* 11/2016 Victor .................... A61K 36/31
2018/0098552 A1* 4/2018 Bhairam .............. A61K 31/352

OTHER PUBLICATIONS

Ostojic, Res Sports Med Oct.-Dec. 2006;14(4):289-99. (Year: 2006).*
Qiu et al., Pharmaceutical Technology Europe—Jan. 1, 2006 vol. 18, Issue 1. (Year: 2006).*

* cited by examiner

*Primary Examiner* — Jean P Cornet
(74) *Attorney, Agent, or Firm* — Kramer & Amado, P.C.

(57) ABSTRACT

This invention discloses a medicinal composition of matter that effectively provide a nootropic effect beyond the effects simple obtain by cannabinoids alone. And, effectively reduce anxiety due to ingestion of xanthines containing oral products.

13 Claims, No Drawings

MEDICINAL COMPOSITIONS OF CANNABINOIDS AND XANTHINES

The present invention relates to oral medicinal compositions of matter containing cannabinoids and xanthines that are bioavailable.

BACKGROUND OF THE INVENTION

Cannabinoids are chemical compounds found in the cannabis plant that interact with receptors in the brain and body to create various effects. Herbal cannabis contains over 100 cannabinoids unique to the plant genus *Cannabis*. The pharmacology of most of the cannabinoids is largely unknown but the most potent psychoactive agent, $^9$-tetrahydrocannabinol ($^9$-THC, or THC), has been isolated, synthesized and much studied due to its abundance and psychoactive attributes. Other plant cannabinoids include: cannabinol (CBN) and cannabidiol (CBD). These and other cannabinoids have entourage effects with THC and may modify its actions when herbal cannabis is smoked.

The most notable cannabinoids include tetrahydrocannabinol ($^9$-THC), cannabidiol (CBD) and cannabinol (CBN). Most cannabinoids derive from cannabigerol-type compounds and differ mainly in the way this precursor is cyclized. The classical cannabinoids are derived from their respective 2-carboxylic acids (2-COOH) by decarboxylation (catalyzed by heat, light, or alkaline conditions).

Like most pharmacologically-active secondary metabolites of plants, THC is a lipid found in cannabis, assumed to be involved in the plant's self-defense, putatively against insect predation, ultraviolet light, and environmental stress.

The actions of THC result from its partial agonist activity at the cannabinoid receptor $CB_1$ ($K_i$=10 nM) located mainly in the central nervous system, and the $CB_2$ receptor ($K_i$=24 nM), mainly expressed in cells of the immune system. The psychoactive effects of THC are primarily mediated by the activation of cannabinoid receptors, which result in a decrease in the concentration of the second messenger molecule cAMP through inhibition of adenylate cyclase.

Cannabidiol has low affinity for the cannabinoid $CB_1$ and $CB_2$ receptors, although it can act as an antagonist of $CB_1/CB_2$ agonists despite this low affinity. Cannabidiol may be an antagonist of GPR55, a G protein-coupled receptor and putative cannabinoid receptor that is expressed in the caudate nucleus and putamen in the brain. It also may act as an inverse agonist of GPR3, GPR6, and GPR12. CBD has been shown to act as a serotonin $5-HT_{1A}$ receptor partial agonist and this action may be involved in its antidepressant, anxiolytic, and neuroprotective effects. It is an allosteric modulator of the μ- and δ-opioid receptors as well. The pharmacological effects of CBD may involve PPARγ agonism and intracellular calcium release.

Cannabinol (CBN) is a mildly psychoactive cannabinoid found only in trace amounts in *Cannabis*, and is mostly found in aged *Cannabis*. Pharmacologically relevant quantities are formed as a metabolite of tetrahydrocannabinol (THC). CBN acts as a partial agonist at the $CB_1$ receptors, but has a higher affinity to $CB_2$ receptors; however, it has lower affinities relative to THC. Degraded or oxidized cannabis products, such as low-quality baled cannabis and traditionally produced hashish, are high in CBN.

Selective breeding of cannabis plants has expanded and diversified as commercial and therapeutic markets develop. Some growers in the US succeeded in lowering the proportion of CBD-to-THC to accommodate customers who preferred varietals that were more mind-altering due to the higher THC and lower CBD content.

It is well known that cannabinoids, especially CBD and THC have many medicinal benefits. The conditions include Post Traumatic Stress Disorder, neuropathic and chronic pain, insomnia, nausea, inflammation, arthritis, migraines, Cancer, Crohn's disease, fibromyalgia, Alzheimer's disease, Multiple sclerosis, Glaucoma, Attention deficit hyperactivity disorder ("ADHD"), sleep apnea and appetite loss, CBD's subtle effects are primarily felt in pain, inflammation, and anxiety relief, as well as other medicinal benefits. CBD also does not have any adverse side effects that may occur with consumption of THC. Unlike THC, CBD also does not cause a high. CBD also appears to counteract the sleep-inducing effects of THC, which may explain why some strains of cannabis are known to increase alertness. CBD also acts to reduce the intoxicating effects of THC, such as memory impairment and paranoia.

Similar to THC, CBN also activates the endocannabinoid system (ECS) to produce its therapeutic effects. In addition to this, like CBD, CBN also stimulates other non-cannabinoid receptors as well. These receptors play a part in modulating several symptoms that contribute to the worsening of anxiety symptoms.

Caffeine is a central nervous system (CNS) stimulant of the methylxanthine class. It is the most widely consumed psychoactive drug. Unlike many other psychoactive substances, it is legal and unregulated in nearly all parts of the world. There are several known mechanisms of action to explain the effects of caffeine. The most prominent is that it reversibly blocks the action of adenosine on its receptor and consequently prevents the onset of drowsiness induced by adenosine. Caffeine also stimulates certain portions of the autonomic nervous system. In addition, caffeine induces ketosis in mammals. At normal doses, caffeine has variable effects on learning and memory, but it generally improves reaction time, wakefulness, concentration, and motor coordination. Caffeine is a proven ergogenic aid in humans. Caffeine improves athletic performance in aerobic (especially endurance sports) and anaerobic conditions. Moderate doses of caffeine (around 5 mg/kg) can improve sprint performance, cycling and running time trial performance, endurance (i.e., it delays the onset of muscle fatigue and central fatigue), and cycling power output. Caffeine increases basal metabolic rate in adults. Caffeine improves muscular strength and power, and may enhance muscular endurance. Caffeine also enhances performance on anaerobic tests. Caffeine consumption before constant load exercise is associated with reduced perceived exertion. While this effect is not present during to exhaustion exercise, performance is significantly enhanced. This is congruent with caffeine reducing perceived exertion, because exercise to exhaustion should end at the same point of fatigue. Caffeine also improves power output and reduces time to completion in aerobic time trials, an effect positively (but not exclusively) associated with longer duration exercise.

Although many health benefits can be derived from caffeine, it can produce anxiety and mild form of drug dependence—associated with withdrawal symptoms such as sleepiness, headache, and irritability—when an individual stops using caffeine after repeated daily intake. Tolerance to the autonomic effects of increased blood pressure and heart rate, and increased urine output, develops with chronic use (i.e., these symptoms become less pronounced or do not occur following consistent use).

Nootropics (colloquial: smart drugs and cognitive enhancers) are drugs, supplements, and other substances that may improve cognitive function, particularly executive functions, memory, creativity, or motivation, in healthy individuals.

In one embodiment, the present invention is novel in that it is formed to provide blends of cannabinoids with xanthine classes of compounds as medicinal dosage forms that are bioavailable, fast acting and highly metabolized, with consistent results that take place in a consistent amount of time.

In another embodiment, the present invention is novel in that it is formed to provide blends of cannabinoids with xanthine classes of compounds which provide a nootropic effect beyond the effects simple obtained by cannabinoids alone.

In another embodiment, the present invention is novel in that it is formed to provide blends of cannabinoids with xanthine classes of compounds which reduces anxiety due to ingestion of xanthines containing beverages.

Optionally, the invention provides a reduction of the side effects associated with the exogenous ingestion of yohimbine and its derivatives.

In another embodiment, the present invention is novel in that it is formed to provide blends of cannabinoids with xanthine classes of compounds which amplify alertness and decrease attention deficit disorders by improving cognitive function, reaction time, focus, energy, and psychomotor vigilance.

BRIEF SUMMARY OF THE INVENTION

The present invention provides medicinal compositions containing cannabinoids and caffeine that are bioavailable.

In one embodiment the composition comprises from 10 to 400 mg of caffeine in combination with one of THC, CBD, CBN or any other cannabinoid or any constituents of Hemp.

In another embodiment the composition comprises from 10 to 400 mg of caffeine or any xanthine, combination with one of THC, CBD, CBN or any other cannabinoid or any constituent of Hemp. As understood herein, Xanthine refers to all xanthines and includes, but is not limited to methylated xanthines (methylxanthines), which include, but are not limited to: caffeine, aminophylline, IBMX (3-isobutyl-1-methylxanthine), paraxanthine, pentoxifylline, theobromine, and theophylline.

Optionally, the composition may include from 1 to 30 mg of yohimbine ($C_{21}H_{26}N_2O_3$—Yohimban-16-carboxylic acid CAS Registry Number: 146-48-5) or a yohimbine derivative. In embodiments including yohimbine, the invention utilizes any yohimbine or yohimbine derivative. In one embodiment, the invention includes yohimbine, Yohimbine HCl, Yohimbine Monoglycine esther, Yohimbine Alkyl Amine, or combinations thereof.

The compositions of the present invention provide medicinal compositions and is related to the administration of the composition thereof to effectively provide a nootropic effect beyond the effects simple obtain by cannabinoids alone. Embodiments of the present invention would provide compositions related to the administration thereof in effectively reducing anxiety due to ingestion of xanthines containing beverages. It may optionally reduce the side effects associated with the exogenous ingestion of yohimbine and its derivatives.

In one embodiment, the present invention is a medicinal composition comprising:

a first active component being Tetracannabinol, cannabidiol, cannabinol, any cannabinoid, constituent of hemp, or combinations thereof; and a second active component being Caffeine or any other xanthine.

In one embodiment, the composition comprises a dose wherein a total of said first active component and said second active component totaling between 10 mg to 730 mg wherein said first active component is present in 1-300 mg/dose and said second active component is present in 1-400 mg/dose In one embodiment, the composition is in the form of a powder.

In one embodiment, the composition is in the form of an orally administrable liquid composition.

In one embodiment, the orally administrable liquid composition further comprises water, fruit juice, yogurt, or pudding.

In one embodiment, the composition is in the form of a powder.

In one embodiment, the composition is in the form of an orally administrable liquid composition.

In one embodiment, the orally administrable liquid composition further comprises water, fruit juice, yogurt, or pudding.

In one embodiment, the invention includes a method comprising: administering an effective amount of the medicinal composition of claim 2 to a mammal in need thereof, wherein said effective amount is between 180-300 mg; and imparting a nootropic effect beyond the effects simple obtain by cannabinoids alone.

In one embodiment, the invention includes a method comprising: administering an effective amount of the medicinal composition to a mammal; and reducing side effects associated with exogenous ingestion of yohimbine and its derivatives.

In one embodiment, the invention includes a method whereby said administering is once a day over a period of treatment of one-eight weeks.

In one embodiment, the invention includes a method whereby the medicinal composition is in powder form and wherein the administering further includes dispersing the composition in water or in a suspension in a suitable aqueous liquid vehicle or carrier to form a liquid composition, and after said dispersing, ingesting orally in a liquid composition, or in a snack composition.

In one embodiment, the invention includes a method whereby the medicinal composition is in powder form and wherein the administering is followed by adding the medicinal composition to a fruit juice, yogurt or pudding.

DETAILED DESCRIPTION OF THE INVENTION

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for describing particular embodiments only and is not intended to be limiting.

The articles "a" and "an" are used herein to refer to one or to more than one (i.e., to at least one) of the grammatical object of the article. By way of example, "an element"

means one element or more than one element. Thus, recitation of "a composition", for example, includes a plurality of the compositions.

In one embodiment, the medicinal composition is in the form of a powder composition. This medicinal composition includes:

tetrahydrocannabinol (THC), or cannabidiol (CBD), or cannabinol (CBN), Caffeine or any other xanthine derivative In an exemplary embodiment, the composition is in the form of a powder. An exemplary serving size of this powder composition is from 10 to 1000 mg of active ingredients, said active ingredients being THC; CBD; CBN, or any other cannabinoid or any constituent of hemp; caffeine or any other xanthine; or combinations thereof.

Optionally, the composition may include from 1 to 30 mg of yohimbine or any of its derivatives.

In an exemplary embodiment, caffeine is present in the powder composition for example in an amount of from 10 mg to 400 mg and yohimbine from 1 mg to 30 mg.

TABLE 1

| INGREDIENTS | Ranges mg/serving |
| --- | --- |
| Caffeine | 10-400 |
| Tetrahydrocannabinol | 1-300 |

Further exemplary suitable ranges within the scope of this disclosure are compositions where caffeine is replaced by other xanthine.

TABLE 2

| INGREDIENTS | Ranges mg/serving |
| --- | --- |
| Theobromine | 10-400 |
| Tetrahydrocannabinol | 1-300 |

The physiologically active compounds contemplated for use herein are included in the medicinal composition in an amount sufficient to produce the desired effect upon the target process, condition or disease. In addition, such compositions may optionally contain one or more agents selected from adsorbents (such as silicon dioxide), flavoring agents (such as peppermint, oil of wintergreen or cherry), coloring agents, preserving agents, and the like, in order to provide pharmaceutically elegant and palatable preparations. Suspensions of the present invention may contain wetting agents, suspending agents, buffers, preserving agents, flavors and sweeteners (sucralose, acesulfame potassium).

As described above, the medicinal composition may, for example, be in powder form. This powder composition can be prepared by premixing THC oil with silicon dioxide, mixing other components in powder form in a suitable blender or planetary mixer and adding the premix of THC and then finally mixing the ingredients for the time necessary to obtain a uniform and homogeneous mixture.

The mixture can then optionally be packaged into jars in a quantity that represents a defined number of servings. A measuring scoop can be added to the jar for the purpose of providing an accurate serving.

The powder composition described above may be ingested orally as a powder composition. In the alternative, a user may scoop a serving of the powder from the jar and mix it with room-temperature water, the powder can also be mixed with any other beverage to provide a suspension. It can also be added and mixed into a fruit sauce, yogurt or pudding.

In one embodiment, the composition comprises 1 to 4.8 grams of medium chain triglycerides per 100 grams of the medicinal composition.

In one embodiment, the invention is directed to a method of providing a nootropic effect in a mammal by administering the composition described above. The mammal may, for example, be a human. The administration can, for example, be oral administration, for example by ingestion of a beverage, fruit sauce, yogurt, or pudding into which the composition described above has been mixed.

The administration may optionally be chronically for a set period-of-time, for example from two to eight weeks. As used herein, "chronically" means repeated ingestion over a period of several days, several weeks, even several months, or longer. Acute (non-chronic) administration may also be utilized. Whether chronically or non-chronic, it is meant that the composition is orally ingested one time per day, either in powder form or mixed with a beverage, fruit sauce, yogurt, pudding, or other liquid composition. The amounts given in Table 1 indicate relative amounts of each component which may be present in a single serving, said single serving optionally being ingested one or more times a day, optionally mixed with a single serving of a beverage, fruit sauce, yogurt, or pudding. The skilled artisan will understand the standard serving size of each of the above.

For example, a single serving of the powder composition as set forth above and as exemplified in Table 1 may be mixed with a single serving of yogurt, for example one cup of yogurt. The same single serving may be mixed with a single serving of pudding, for example one half cup. An exemplary serving size for water or a beverage with which the single serving powder composition may be mixed would be eight ounces.

In a specific embodiment, the subject invention provides aqueous compositions into which the powder composition has been mixed, suitable for oral administration to mammals including, without limitation, humans. To prepare a composition according to one embodiment of the invention, a desired amount of each component of the composition is added to a selected volume of water or beverage, and sufficient stirring is effected to cause a dispersion of the powder composition to create an aqueous composition.

A composition according to this invention may also include other ingredients such as, for example, flavoring agents, colorants, viscosity modifiers, preservatives, chelating agents, antioxidants, surface modifiers and other medicinal adjuvant materials. Other materials include any substance that is generally recognized as promoting the health or function of a mammalian organism, including humans, or benefiting a composition useful thereof in terms of its efficacy, appearance, stability, consistency, aroma, or viscosity. Such substances include, for example, other amino acids and their salts, vitamins, minerals, fatty acids, enzymes, mono-glycerides, di-glycerides, tri-glyceride ester oils (including, for example, vegetable oils and animal fats) emulsifiers, hydrolyzed proteins, whey protein, stabilizers, flow modifiers, viscosity improvers, chelating agents, enzymes, and surfactants (whether anionic, cationic or nonionic). The total amount of these materials in a composition can be any amount between about 0.01% and about 50% by weight based on the total weight of said composition, including all percentages and ranges of percentages therebetween.

A composition according to this invention may also comprise one or more natural or synthetic beverages. For example, a natural beverage may contain the pulp, juice or any other constituent of a naturally-occurring fruit, vegetable, or animal product whether from the wild, cultured, cultivated on a farm or otherwise domesticated.

Natural beverages include, without limitation, materials such as milk products, soy products, ice cream, yogurt, citrus fruit juices, non-citrus fruit juices, and vegetable juices, or components of any of the foregoing, wherein said natural beverages are present in any effective amount to impart flavor to the compositions, which may be any amount between about 0.1% and about 99% by weight based on the total weight of said composition, including all percentages and ranges of percentages there between.

Thus, it is evident that a composition according to this invention may be made quite palatable to a mammalian subject, including a human. Serving sizes may be any serving size in the range of about 10 milligrams to about 50 grams, in an aqueous solution that is from about 20 ml to about 2,500 ml in volume. Thus, for example, 10 milligrams to about 50 grams of the powder composition described above may be mixed with 20 ml to about 2,500 ml of water, juice, or other liquid composition, in particular 100 mL of water, juice, or other liquid composition. This admixing creates the oral composition which may be taken as set forth above. Such oral composition can provide a concentrate from which the required amount of each component may conveniently be provided.

The compositions of the subject invention can be formulated for a variety of modes of administration. These formulations include, but are not limited to, compositions for oral administration, emulsion compositions, gel formulations, oral solid compositions, and oral liquid compositions, or with protein.

It has been found that oral administration of the medicinal compositions according to the invention are effective provide a nootropic effect beyond the effects simple obtain by cannabinoids alone. Embodiments of the present invention would provide compositions related to the administration thereof in effectively reducing anxiety due to ingestion of xanthines containing beverages.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

The invention claimed is:

1. A medicinal composition comprising:
a first active component consisting of 10 to 400 mg/dose of tetrahydrocannabinol, cannabidiol, cannabinol, or a mixture thereof,
a second active component consisting of 1 to 300 mg/dose of caffeine, theobromine, or a mixture thereof; and
a third active component consisting of 1 to 30 mg/dose of yohimbine, yohimbine HCl, yohimbine monoglycine ester, yohimbine alkyl amine, or a mixture thereof;
wherein the first active component, the second active component, and the third active component are the only active ingredients present in the medicinal composition.

2. A medicinal composition according to claim 1, wherein the composition is in the form of an orally administrable liquid composition; wherein the first active component is made by mixing THC oil with silicon dioxide.

3. The medicinal composition of claim 1, wherein said composition is in the form of an orally administrable liquid composition.

4. The medicinal composition of claim 2, wherein said orally administrable liquid composition further comprises water, fruit juice, yogurt, or pudding.

5. The medicinal composition of claim 1, wherein said composition is in the form of a powder.

6. The medicinal composition of claim 1, wherein the medicinal composition further comprises water, fruit juice, yogurt, or pudding.

7. A method for treating pain, inflammation, anxiety, post-traumatic stress disorder, insomnia, nausea, arthritis, migraines, Crohn's disease, fibromyalgia, Alzheimer's disease, multiple sclerosis, glaucoma, attention deficit hyperactivity disorder ("ADHD"), sleep apnea or appetite loss, comprising the steps of: administering an effective amount of the medicinal composition of claim 1 to a mammal in need thereof, wherein said effective amount is between 180-300 mg; and imparting a nootropic effect beyond effects simply obtained by cannabinoids alone.

8. A method for treating pain, inflammation, or anxiety, stimulating the autonomic nervous system, or improving athletic performance, the method comprising administering an effective amount of the medicinal composition of claim 1 to a mammal; and reducing side effects associated with exogenous ingestion of yohimbine compounds.

9. The method of claim 7, wherein said administering is once a day over a period of treatment of one-eight weeks.

10. The method of claim 7, wherein the method includes, prior to said administering, providing said nutritional composition is in a powder form; dispersing the composition in water or in a suspension in a suitable aqueous vehicle or carrier to form a liquid composition; and the administering followed by orally ingesting said liquid composition, or in a snack composition.

11. The method of claim 7, wherein the medicinal composition is in powder form and wherein the administering is followed by adding the medicinal composition to a fruit juice, yogurt or pudding.

12. A beverage comprising a suspension of a medicinal powder composition in an aqueous carrier, wherein the powder comprises:
a first active component comprising 10 to 400 mg/dose of tetrahydrocannabinol, cannabidiol, cannabinol, or a mixture thereof,
a second active component comprising 1 to 300 mg/dose of caffeine, theobromine, or a mixture thereof; and
a third active component consisting of 1 to 30 mg/dose of yohimbine, yohimbine HCl, yohimbine monoglycine ester, yohimbine alkyl amine, or a mixture thereof;
wherein the first active component, the second active component, and the third active component are the only active ingredients present in the medicinal composition;
wherein the first active component is made by mixing THC oil with silicon dioxide.

13. A dispersion in a liquid medium of a medicinal composition comprising:
a first active component consisting of 10 to 400 mg/dose of tetrahydrocannabinol, cannabidiol, cannabinol, or a mixture thereof, a second active component consisting of 1 to 300 mg/dose of caffeine, theobromine, or a mixture thereof; and a third active component consisting of 1 to 30 mg/dose of yohimbine, yohimbine HCl, yohimbine monoglycine ester, yohimbine alkyl amine, or a mixture thereof;

wherein the first active component, the second active component, and the third active component are the only active ingredients present in the medicinal composition.

* * * * *